(12) United States Patent
Riss et al.

(10) Patent No.: US 6,168,921 B1
(45) Date of Patent: Jan. 2, 2001

(54) METHOD FOR THE QUANTITATIVE AND/OR QUALITATIVE DETERMINATION OF ATOMS OR MOLECULES

(76) Inventors: Udo Riss, Feldstr. 14, D-23909 Ratzeburg; Dietmar Meineke, Im Raum 8, D-22946 Trittau, both of (DE)

( * ) Notice: Under 35 U.S.C. 154(b), the term of this patent shall be extended for 0 days.

(21) Appl. No.: 09/198,298

(22) Filed: Nov. 23, 1998

Related U.S. Application Data

(63) Continuation-in-part of application No. 08/895,624, filed on Jul. 17, 1997, now abandoned.

(30) Foreign Application Priority Data

Jul. 19, 1996 (DE) .............................................. 196 29 243

(51) Int. Cl.[7] .......................... C12Q 1/68; G01N 21/00; G01N 21/76; G01B 9/02; G02B 1/10

(52) U.S. Cl. .................. 435/6; 422/55; 422/57; 422/58; 422/82.11; 435/7.2; 435/7.3; 435/7.32; 436/172; 436/518; 436/524; 356/345; 356/937; 359/580; 359/586; 359/589

(58) Field of Search .................. 422/55, 57, 58, 422/82.11; 435/6, 7.2, 7.3, 7.32; 436/172, 518, 524; 356/937, 345; 359/580, 586, 589

(56) References Cited

U.S. PATENT DOCUMENTS 5,418,136 * 5/1995 Miller et al. ............................. 435/5
5,541,057 * 7/1996 Bogart et al. ............................. 435/5

OTHER PUBLICATIONS

"Zur Transmissionsellipsometrie optisch anisotroper Komponenten und Systeme", Udo Riss, Universitat–Gesamthochschule Kassle D–34, pp. 55–73 with English translation.

"Neuer Immunologischer Test mit Laserlicht," Jun. 1996 Biospectrum, Riss et al, Industrie–Applikationen, pp. 53–54 With English language translation.

* cited by examiner

*Primary Examiner*—Rodney P. Swartz
(74) *Attorney, Agent, or Firm*—Jacox, Meckstroth & Jenkins

(57) ABSTRACT

Receptor molecules are anchored on a solid or fluid flat substrate, these being able to selectively bind other atoms or molecules. The substrate surface is then ellipsometrically measured in that the change of the state of polarization, undergone by the linearly polarized light with the reflection on the substrate, is acquired. Subsequently, the substrate with the receptor molecules anchored thereon, for coupling the atoms or molecules to be determined, are exposed to the latter, after which an ellipsometrical measurement is again effected. The changes in the state of polarization are compared to values evaluated by way of reference samples, after which a qualitative and quantitative determination of the coupled atoms or molecules is effected.

20 Claims, 2 Drawing Sheets

METHOD FOR THE QUANTITATIVE AND/OR QUALITATIVE DETERMINATION OF ATOMS OR MOLECULES

CROSS REFERENCE TO RELATED APPLICATION

This application is a continuation-in-part of Ser. No. 08/895,624 filed Jul. 17, 1997, now abandoned.

BACKGROUND OF THE INVENTION

The invention relates to a method and system for measuring the binding reactions of atoms or molecules to other atoms or molecules which are locked to a surface.

A quantitative and qualitative acquisition of atoms and molecules is becoming nowadays more and more important. Particular in medical technology, biotechnology and pharmaceutical technology such methods are for example employed for the acquisition of antigen/antibody complexes on solid or fluid phases. For in vitro diagnosis of various diseases, one uses the specific bonding characteristics of antibodies to their antigens. The analysis, in particular ascertaining certain molecules and the quantitative determination of these molecules, gives information for example on the immune status, the course of a disease, the deficiency or excess of body-specific substances, defects in genetic material and much more.

Known methods of this type at the present time function such that with the help of physical and/or chemical methods, antibodies or antigens for example of complex material mixes are selectively bound and then are directly or indirectly detected or quantified. Examples for this are the determining of immune globulins in body fluids, determining antibodies to infectious diseases (IGG, IGA, IGM), determining antibodies involved in allergies (IGE, IGG, IGM), determining auto-immune antibodies involved in immune diseases, for example, rheumatism, determining proteins and peptides, determining polyclonal and monoclonal antibodies, hormones, determining breakdown products or secretions for example as disease indicators, determining substances foreign to the body, e.g medication, drugs, environmental chemicals.

The methods currently employed in medical technology are apparatus-extensive, time consuming, partly highly complicated, and with regard to their discrepancy, have certain risks. These known methods work essentially according to the principle that firstly molecules which can selectively bind other molecules or atoms, for example antigens, may be bound onto a solid phase as a substrate. After an incubation with which all molecules concerned are bound onto the solid phase, the excess or non-bound material is removed by way of one or more washing steps. Then this solid phase, adhered with molecules for selective bonding (for example, antigens) is exposed to the sample to be examined.

According to the lock-and-key principle, the molecules or atoms located in the sample (for example, antibodies) are bound to the molecules/antigens of the solid phase, in as far as they are present (primary bonding). After an incubation, after which all molecules concerned are bound, then again the removal of the excess non-bound material is effected in one or ore washing steps. Where appropriate, then for strengthening, a further antibody of animal origin is added, which is directed against the substance in question. After the incubation has been effected then, again, the removal of excess non-bound material is effected in one or more washing steps.

Finally, by way of the addition of previously marked molecules (e.g., by way of enzymes, radioactive substances, light emitting substances or likewise), a qualitative or quantitative detection of primary bondings is effected by activatable conditions which can be measured. For this too, again an incubation is required as well as subsequently one or more washing steps in order to remove excess material. After such, an effected marking of the whole complex, the complex directly, or where appropriate, after an addition of a reagent, undergoes a measurement which gives insight on the type and quantity of the bound molecule, for example, the antibodies which are to be acquired.

The variation of measuring methods is likewise as large as the variation of method steps. Common to all, however, is a comparatively lengthy duration which is determined by the addition steps and the incubation. In practice, such methods require procedural times in the range of a few hours to several days. Due to the numerous different method steps and with this, the method parameters which are partly to be kept within small tolerances, such examinations as a rule can be only carried out by well qualified personnel.

Moreover, the quality of the results depends on the sum of the qualities of all the method steps. This causes the known methods to have a relatively high inaccuracy since the tolerances of the individual method steps acccumulate.

Yet another problem is that the test methods are designed such that the molecules bound on the solid phase are only provided for bonding to a molecule class, so that, for example, for recording various immune globulins various other methods must be carried out to bring about a good measurement. With regard to this the following literature is referred to:

R. H Burdon, P. H. van Knippenberg, eds.: Laboratory Techniques in Biochemistry and Molecular Biology, Vol.15; Elsevier Science Publishers B. V., Arnsterdam, New York, Oxford; 1988.

L. Hudson, F. C. Hay: Practical Immunology; Blackwell Scientific Publications, Oxford, London, Edinburgh, Melbourne, 1980.

Aside from the enormous time consumption, apparatus requirements and personnel intensive effort required by these known methods, there arises a considerable amount of waste (in particular, chemical or radioactive contaminated waste) which must be partly disposed of as special waste. The active substances, in fluid form, to be used with these methods are often unstable and must be protected from microbial infection. The energy consumption too is not inconsiderable, since the incubation steps as a rule must be carried out at body temperature, that is at 37 degrees Celsius and usually the apparatus must be kept at this temperature day and night. For a long time, one has been striving for a more simple and reliable test method.

A way which, at its beginning, seemed to hold out some promise was biosensory analysis. Biosensory analysis used semiconductors which determined a change of electrical characteristics of the molecules deposited on the substrate material as a basis for determining molecule bonding. However, this methodology has not brought the expected success because the changes of electrical characteristics occurring by way of selective molecule bonding are either not particularly significant or can only be measured inadequately. Therefore, in practice, such methods of biosensory analysis functioning on a semiconductor basis have only been carried out for two component systems in a limited manner. But these methods too are not very accurate. The semiconductor base required as the substrate has to be disposed of. What is needed, therefore, is an accurate and simple method and procedure for measuring binding reactions of atoms or molecules.

SUMMARY OF THE INVENTION

Against this background it is the object of the invention to provide a quantitative and/or qualitative determination of atoms and molecules with which, with comparatively little technical apparatus expenditure, this determination may be carried out simply and with a high reliability.

Accordingly, the invention provides for anchoring on a solid or fluid flat substrate, such molecules known per se it may also concern atoms with special applications, which are in the position to selectively bind other certain molecules or atoms these molecules are hereinafter described as receptor molecules. The substrate provided with these receptor molecules is then irradiated with electromagnetically polarized waves wherein the preferably reflected but also where appropriate the beamed through waves are received and acquired with regard to their state of polarization by way of a suitable device. Subsequently, the substrate with the receptor molecules anchored thereon are exposed to the material to be examined, for example, a blood sample. Afterwards, the substrate with the receptor molecules anchored thereon, as well as where appropriate the further molecules (ligands) or atoms bound in this way, are exposed to the electromagnetically polarized waves, whereafter again the reflected or where appropriate, also the beamed through waves are received and their state of polarization in comparison to the previously determined state of polarization is acquired. The change in the state of polarization, by way of reference values previously evaluated by reference samples, gives a direct indication on the type and numbers of coupled molecules or atoms. Those molecules to be determined from the sample may be anchored on the substrate as receptor molecules. The selective bonding is then effected to so called marker molecules.

The previously described manner of method may be modified with respect to measuring technology in that the first measurement of the substrate provided with receptor molecules or atoms is omitted and in its place, from another sample which is not incubated or is incubated with a known reference sample, corresponding values for the first measurement are evaluated or calculated. In this case, although in the physical sense no measurement is carried out, the corresponding required values are evaluated however in an indirect manner.

The method of ellipsometry has been known for some time, in this context the book given the title 1' Selected Papers on Ellip5 ryfV by R. M. A. Azzam which appears in the SPIE Optical Engineering Press, U.S.A., under ISBN 0-8194-0570-1, is referred to. The method according to the invention which may be carried out with a commercially available ellipsometer, may be carried out speedily and comparatively simply. It functions highly accurately since the commercially available ellipsometer may evaluate to a high degree of accuracy, the polarization condition, in particular the change in polarization of the received waves in comparison to the emitted waves. Thus, the change in polarization may be determined with for instance an accuracy of:

$\leqq 0.002°$ in the $\Delta/\Psi$ diagram (from these values, in the known manner, the refractive index and the layer thickness may be numerically evaluated) As such, for example, layer thicknesses of layers of submonolayers can be detected, which in the statistical mean are a thousand times thinner than the diameter of the hydrogen atom. The method according to the invention functions with a corresponding accuracy, such that at present sensitivities in the region between 0.01 and 0.1% are achieved.

The method according to the invention is preferably carried out with an approximately linearly polarized light (slightly elliptical) which is preferably emitted from a laser, since then no separate filtering for maintaining polarized light is required. The evaluation is preferably effected on the basis of waves reflected on the substrate with the help of a photo diode with a polarization prism arranged in series which be rotated highly accurately about defined angular steps by way of a stepper motor. Such an ellipsometer construction is known per se, and in this context the submonolayer ellipsometer of the type description EL X-1 of DRE-Dr. Riss Ellipsometerbau GmbH in D-23909 Ratzeburg, Germany is referred to. With a suitable choice of receptor molecules to be anchored on the carrier the method may be applied for practically any biological, medical or pharmaceutical tests. The receptor molecules to be anchored on the substrate are merely to be chosen such that they are in the position to selectively bind the atoms, molecules or molecule groups to be detected. The method according to the invention, due to its very high accuracy, is also in the position to solve much more complicated cases, i.e. to determine one two or more substances to be detected with only one method.

The method according to the invention has considerable advantages in the field of previously mentioned biomedical test methods. To be mentioned is the higher sensitivity to powers of ten in comparison with the known methods, a reduced material consumption, noticeable time saving, considerably reduced costs, much reduced environmental degradation and not lastly a noticeably reduced development effort for new tests. The material consumption at present lies at about 0.2 $\mu$for the receptor molecules to be anchored on the substrate as well as the sample material to be tested. The previously mentioned costly washing steps may for a large part be dispensed with, secondary incubations and detections are no longer required. The analysis of various analyte types is also possible with only one method step. The actual ellipsometrical measuring period lies in the region of seconds, the incubation required may for example be limited to 10 minutes. The number of analyses is at the same time not limited and the process can be fully automated. Since, by way of the method according to the invention, for the detection of allergies, diseases and likewise, only antigens and antibodies directed against these need be present, the search for antibodies which are directed against primary antibodies and modified antibodies which are directed against secondary antibodies may be omitted. In this way, the development cost for new tests may be considerably reduced.

The method according to the invention may be adjusted in its sensitivity to practically any level in that the sample to be measured is either added immediately to molecules (e.g. antibodies or antigens) which bind with the molecules to be measured even before the actual coupling process, or, similar to the ELISA test, an additional incubation with molecules (e.g. antibodies) is effected. This additional coupling process is advantageously applied for increasing the sensitivity. The purpose lies in changing the size and the optical characteristics (e.g. the refractive index) of the receptor molecules or molecule complexes. This method manner is particularly useful with small molecules or with a low molecule concentration in the sample in order to increase the sensitivity of the method.

The method according to the invention is not limited to the previously mentioned application cases, it is suitable for determining the type and quantity of a multitude of biological and chemical reactands. In this context one must point out the ellipsometric detection of immune globulins, of auto-immune antibodies, of proteins or peptides, of DNA's (deoxyribonucleic acid) as well as RNA's (ribonucleic acid), of receptors or their activators on or in biological membranes as well as of molecules or their bonding partners on or in artificial membranes.

DETAILED DESCRIPTION OF THE INVENTION

Figure 1:
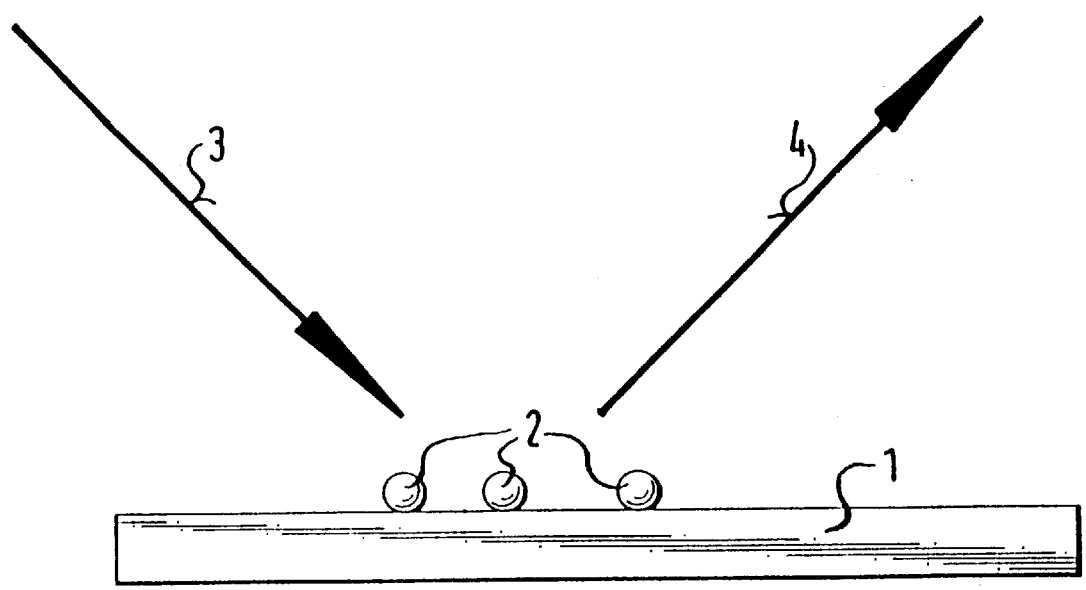
FIG. 1 is a schematic view illustrating light directed to a substrate.
Figure 2:
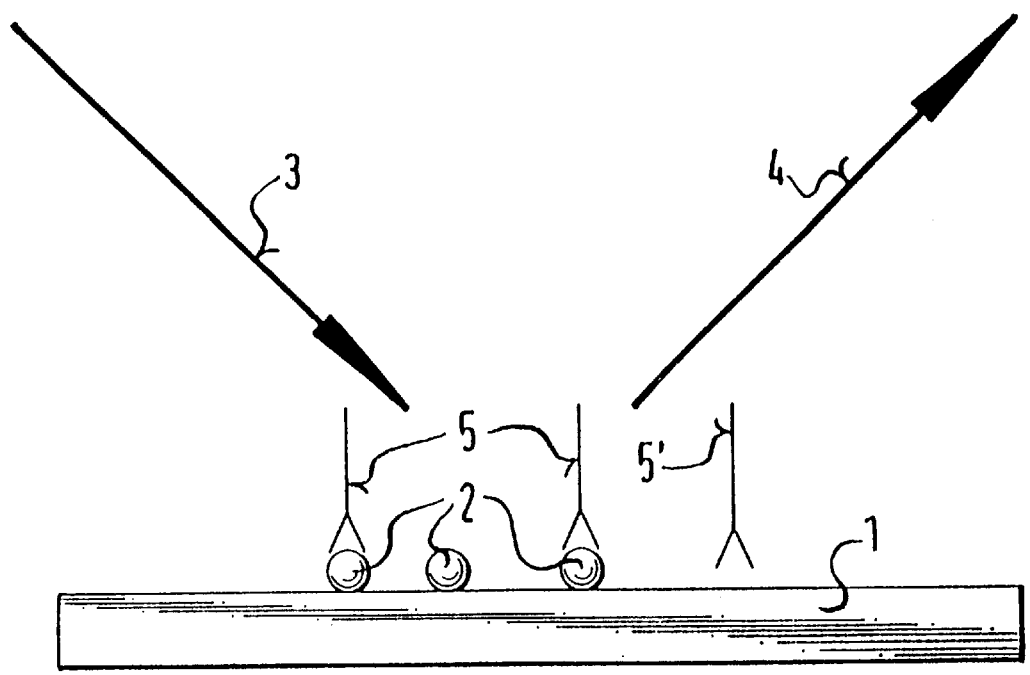
FIG. 2 is a schematic view showing receptor molecules 2, bound molecules and non-bound molecules.

Hereinafter, a general description of a method is described by way of FIGS. 1 and 2 according to the invention. On a flat substrate 1, receptor molecules 2 are firstly anchored which are in the position to selectively bind certain molecules or atoms (so-called ligands). These receptor molecules 2 are bound onto a solid or liquid phase of the substrate 1 and subsequently subjected to a first ellipsometric examination. Specific receptor molecules 2 are bound to the substrate 1 using a conventional enzyme linked immunosorbent assay or ELISA-test which are able to create such bindings.

The next step comprises blocking with molecules so that there is no unspecific binding to the surface 1. This may also be effected using conventional ELISA-tests.

After a washing process (and drying) of the prepared substrate 1, a first measurement takes place. The washing process must be reproducible and must be carefully performed so that specific bindings are not removed. A typical washing process works as follows. A small quantity (1 $\mu$l) of washing buffer is put on the sample and removed after a time of about 1–10 seconds. This procedure is made, for example, three times. Alternatively, a washing buffer can be caused to flow over the sample. The flow and volume of this washing buffer must be well defined and should not exceed a test specific limit. That means if the volume of the washing buffer is too big or the pressure of the flow is to high, sensitivity goes down significantly. Additional to this, too high pressure has an influence on natural anisotropy of the sample. On the other hand, the volume of the washing buffer must be big enough to reduce unspecific bindings.

The measurement is made at a well defined position on the sample. The sample itself is in a holder which brings no stress into the sample. Mechanical stress would influence measurement signals and would cause errors. The external induced stress should be stable at $10^{-6}$ N/mn$^2$ otherwise it would influence the measurement. The first measurement takes about 2–4 seconds. Measured are ellipticity and orientations of the light beam reflected from the sample. Alternatively, the ellipsometric quantities $\Delta$ and $\Psi$ can be measured. [The use of a comparison ellipsometer which gives only the change of intensity as result is not possible.] The measurement is used to get a reference value for the prepared substrate. The sample shows a slight anisotropy. This anisotropy normally makes it necessary to measure two quantities. The sample anisotropy depends on the type and treatment of the sample. However, each natural sample shows anisotropy when measured with high precision submonolayer ellopsometry.

The sample is incubated simply by dropping the test substance in a defined way on the sample. Incubation takes place at room temperature or at about 37° C. The incubation time depends on the sample. It starts at a few seconds and can reach 30 minutes. This depends on the molecular size. Small molecules need less incubation time than bigger ones. The sample is incubated and then washing a second measurement takes place. The second washing and measurement process is similar to the first one. The second washing process can be integrated into the measurement process if measuring in a cell. So it is not necessary to make an explicit washing. With the data from the measurements, it is possible for him to make measurements of the binding reactions of atoms using the techniques taught in the doctoral thesis "Zur Transmissions ellipsometrie optisch anisotropher Komponenten und Systeme" which is incorporated herein by reference and made a part hereof. In this doctoral thesis it is not taught how to measure and to calculate molecular bindings. Only mathematics how to calculate anisotropy in general is shown. Especially mathematics to calculate anisotropic multilayer resonators can be used for calculation. In reality we have no multilayer system, because only a small number of molecules is locking. If no closed layer is there then we normally cannot calculate with layer systems. However, we have found that mathematics is also valid for molecular locking. The reasons for this must be the diffraction of light. We transformed the experience made with glass to the samples used for the invention. That means, in the above-mentioned doctoral thesis, it was found that glass has complex photoelastic coefficient which was measured in transmission, so we concluded that our samples must have similar behavior when measuring in reflection. This is the reasons for the spirals being measured. The form of the spirals depends on the anisotropy of the sample and the molecules. If anisotropy would not be there, then we would measure no spirals.

At the same time the substrate with the receptor molecules 2 located thereon are fixed to a sample holder of an ellipsometer (not shown), after which approximately linearly polarized light 3 which, for example, comes from a helium-neon laser, is directed onto the substrate 1 in a predefined angle which is oblique to the surface of the substrate 1.

The light 4 reflected from the substrate 1 is led to a photo-diode (not shown) via a polarization prism (not shown). The polarization prism is rotatable about the longitudinal axis of the reflected light beam 4 in order to determine the axes and ellipticity of a polarization ellipse defining a state of polarization of the reflected light beam 4. Proceeding from the given state of polarization of the incident light beam 3, a phase and amplitude change of the light 4 reflected from the substrate 1 with the layer of receptor molecules 2 located thereon is evaluated. With these values, a refractive index and the mean layer thickness of the receptor molecules 5 may be determined.

Then the substrate may be exposed to the material to be examined, for example a blood probe, and this being over a certain incubation time. Within this time, the receptor molecules 2, as far as are present in the sample, selectively bind atoms or molecules 5 according to the lock-and-key principle, these atoms or molecules then leading to a change in the layer located on the substrate. After incubation, the substrate undergoes a washing procedure in order to remove the non-bound molecules 5. By way of renewed ellipsometric measurement, these changes are then acquired with respect to the prior measurement and compared by way of reference values evaluated from reference samples. Additional to this, mathematics for describing anisotropic resonance systems which is taught in the doctoral thesis "Zur Transmissions ellipsometric optisch anisotroper Komponenten und Systems", which is incorporated herein by reference and made a part hereof, can be used for calculation of theoretical functions. Since different molecules which couple onto the receptor molecules form layers of different optical reflection characteristics, with a suitable concept of the method, as a rule first it can be qualitatively determined whether and where appropriate which molecules 5 have been bound to the receptor molecules 2. Furthermore, in general quantitative information can be made, that is on the quantity of the bound molecules 5.

With the previously described method urine of a patient for example may be tested for albuminuria (secretion of albumin with urine). With albuminuria protein is secreted with the urine. A positive result may indicate diseases of the kidney tissue or a blocked kidney for example with heart insufficiency. With inflammation of the renal pelvis and the bladder leucocytes and erythrocytes likewise lead to a positive protein result. Thus, according to the disease albumin, globin and other blood-protein bodies must be differentiated. At the same time there must be recognized harmless albuminuria, for example after exceptional physical exertion, with which cells or cell fragments appear in urine.

With the method according to the invention this may be acquired as follows. Firstly a suitable substrate with an activated solid phase of cobalt-activated polystyrene is selected which physically bonds polar molecules. Onto this substrate the urine sample is then placed. After an incubation time of 5 minutes, albumins, other proteins such as globulins and protein-containing cell fragments and cells rigidly bind to this solid phase comprised of cobalt-activated polystyrene. Here then, the searched molecules themselves form the receptor molecules. The substrate thus created is then ellipsometrically measured. The polarization-ellipsometric parameters, orientation and ellipticity, or $\Delta$ and $\Psi$ are acquired and stored. Then, individually or mixed, marker molecules (e.g. mono or polyclonal antibodies) are added to the substrate carrier, these then specifically bonding to certain proteins or cell membrane structures. Seen in reverse, the proteins anchored to the substrate as receptor molecules are in the position to selectively bind these marker molecules. After an incubation of 5 minutes, a renewed ellipsometric measurement is effected, wherein from the differences of both measurements on the one hand it may be qualitatively determined which marker molecules have settled down, and on the other hand quantitatively, the magnitude with which the marker molecules have settled down. By way of data which is stored and has been acquired previously from reference samples, the qualitative and quantitative determination of the marker molecules and thus finally, in this case, the receptor molecules of interest (the proteins), may be made, by which means indications on the type of disease are possible.

As the previously mentioned embodiment example shows, it is of no consequence for the method according to the invention whether the material to be tested is bound as a receptor molecule or as a molecule (ligand) which reacts with the receptor molecule. In each case here, the method is to be modified in a suitable manner.

A brief description of the procedure of the invention will now be described.

Figure 4:
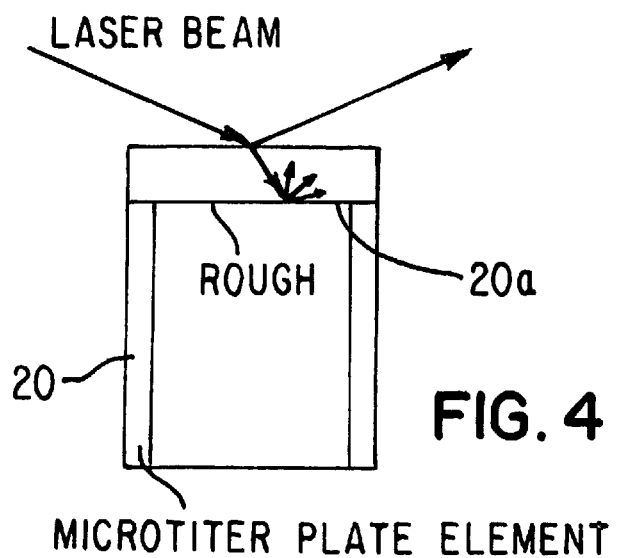
FIG. 4 is an illustration showing a microtiterplate having a backside which is made rough.

First, one or more ELISA-microtiterplates 20 (FIG. 4) are made rough on a side 20a thereof where normally the liquid is filled in so that there is only a reflection from the side were the molecules are bound. The light which goes through the material of the microtiterplate is not reflected from the backside 20a of the microtiterplate, because the backside 20a is made rough. Each ELISA-microtiterplate 20 is used from the backside 20a. These microtiterplate are a product available from Nunc Company of Denmark.

In the next step, about 2 $\mu$of a liquid antigen solution which is in the range of, for example, 1–10 ng/ml, but it should be appreciated that other concentrations are also acceptable is put on the backside of each microtiterplate. One suitable liquid antigen solution may be Cladosporium herbarum obtained from Mast Diagnostica GmbH of Reinfeld, Germany.

After an incubation time of about 15 minutes the microtiterplates are washed with a commercial washing solution (0,20%) TWEEN 20; 0,0025% Thimerosal). Next, a blocking is done with herbum serum albumin or "HSA". In the embodiment being described, "blocking" comprises another type of molecule to bind to all available free binding possibilities on the sample carrier which in this embodiment is polystyrene. After this first washing step, a second washing is performed in the same manner and then the microtiterplates are dried by waiting.

After a first measurement is made with the ellipsometer (not shown). The measurement is made at a well defined position so that the second measurement is done exactly at the same place. Great care is taken relative to the alignment of the sample, especially the angle of the incidence which must be very exact.

Next, a sample serum (about 2 $\mu$l) is put on the substrate 1. For example, a human blood serum may be used or calibration standards which are available from Mast Diagnostic GmbH, Germany. After an incubation time of 15 minutes at 37° C., the substrate 1 is washed in the manner described above. After the substrate 1 is dry, a second measurement is taken with the ellipsometer.

Figure 3:
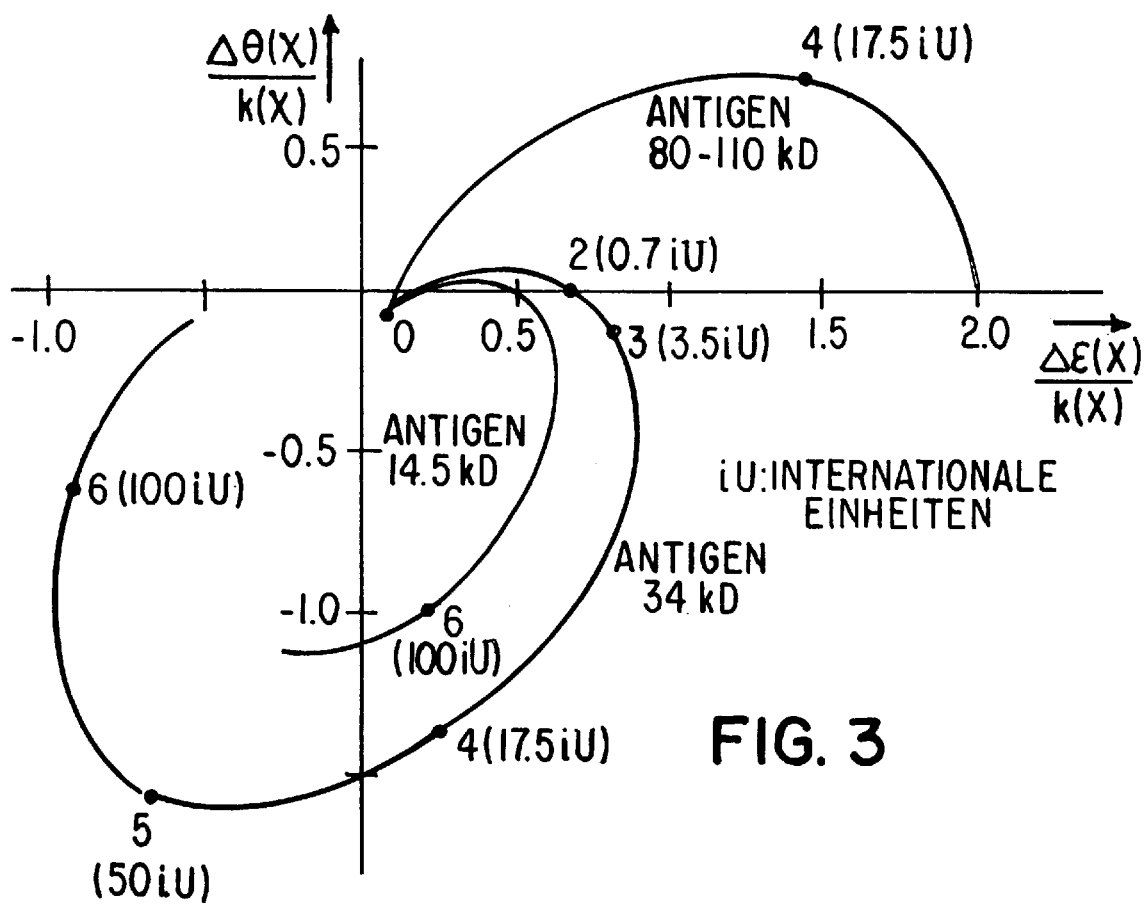
FIG. 3 is a graphical illustration showing measurement of binding reactions of antibodies with antigens of different size.

Both measurement information is put into computing means or a computer program (not shown) which determines or calculates the number of molecules locked to the surface of substrate 1 by taking the anisotropy of the solid phase. The spirals of FIG. 3 illustrate the l anisotropy. FIG. 3 shows measurement results made with antigens of different size. $\Delta\epsilon(\chi)/k(\chi)$ describes the change in orientation of the reflected laser beam in relation to a constant $k(\chi)$ which depends on the incoming polarization $\chi$. $\Delta\Theta(\chi)/k(\chi)$ is the corresponding value for the ellipticity of the reflected light. It can be seen clearly that the measured curves show spirals which depend on the size of the antigen molecules. These spirals are caused by anisotropy. The basic formulations used by computing means of the computer program for calculation of anisotropy effects, such as complex photoelasticity and anisotropic layer effects, are described in the German Doctoral Thesis, "Zur Transmissions ellipsometric optisch anisotroper Komponenten und Systeme" Inauguraldissertation zur Eriangung des akademischen Grades Doktos-Ingenieurs (Dr.-Ing.) Im Fachbereich Maschinenbau der Universitat-Gesamthoschschule Kassel, D44, 1998. All of which are incorporated herein by reference and made a part hereof. We now have a resolution of up to 50–200 molecules which is significantly better than methodologies suggested by the prior art.

A second example of a measurement of biotinzed antibodies to a Streptavidin surface in accordance with the invention will now be described. First, a plurality of Elisa Microtiter plates (see comments above) are prepared as described earlier herein.

A streptavidin is locked to the substrate 1 surface by putting a drop of the microtiterplate and waiting for minutes. With bovine serum albumin ("BSA") or human serum albumin ("HSA"), the surface becomes blocked. It is important that no molecules (such as sugar), which can go from the streptavidin substrate 1 into a liquid, are used. In the embodiment being described, the liquid may comprise a blood serum sample or any kind of buffer which may include any kind if liquid which comes into contact with the substrate. After this step, a first washing is performed.

Now the sample is put into a small cuvet (not shown). The sample solution is a buffer solution which may comprise any buffer which does not destroy the biotinized antibodies is usable with biotinzed-antibodies filled into the liquid, and a measurement in accordance with the invention is started, thereby resulting in kinetic of the locking process.

A measurement and calculation is then performed in the manner described above. The locking of molecules are calculated in the manner described earlier herein. The sensitivity of the measurement was, in the embodiment being described, by a factor 1000 to 20000 times more sensitive than measurements, for example, of a traditional surface plasmon analysis. We are now able to measure the locking of 50 and 600 molecules in minimum. The incident polarization is made so that the reflected polarization shows nearly minimal possible ellipticity. The point of minimal ellipticity is not used because this would cause errors by depolarization. In this case we measured with different anitobody-concentrations, so that we can use them as reference for the calculation of theoretical curves.

While the methods herein described, and the forms of apparatus for carrying these methods into effect, constitute preferred embodiments of this invention, it is to be understood that the invention is not limited to these precise methods and forms of apparatus, and that changes may be made in either without departing from the scope of the invention, which is defined in the appended claims.

What is claimed is:

1. A method for the quantitative and/or qualitative determination of atoms or molecules from a sample, wherein the following method steps are to be carried out after one another:
    a) atoms or molecules are anchored on a solid or fluid flat substrate, these atoms or molecules being able to selectively bind other molecules or atoms,
    b) electromagnetically polarized waves are transmitted onto the substrate which is provided with said anchored atoms or molecules,
    c) the waves, reflected by the substrate which is provided with said anchored atoms or molecules, or beamed through, are received,
    d) at least a part of the state of polarization of the received waves is evaluated,
    e) the substrate with said anchored atoms or molecules anchored thereon, for coupling of said atoms or molecules from said sample to be measured, is exposed to said sample atoms or molecules from said sample,
    f) the method steps b) to d) are again carried out, the change in the state of polarization in comparison to that previously evaluated is acquired, and by way of the evaluated reference values the number and/or type of coupled atoms or molecules is determined without use of an interference film;
    wherein step f) comprises the steps of:
    direct or indirect measuring the optical anisotropy before molecules from said sample have locked but after the surface is coated with receptor molecules;
    direct or indirect measuring optical anisotropy for a different number of locked molecules from said sample;
    using the measured values to calculate the evaluated reference values.

2. A method for the quantitative and/or qualitative determination of atoms or molecules, wherein the following method steps are to be carried out after one another:
    a) atoms or molecules are anchored on a solid or fluid flat substrate, these atoms or molecules being able to selectively bind other molecules or atoms,
    b) the substrate with said anchored atoms or molecules anchored thereon, for coupling of atoms or molecules to be determined, is exposed to the latter,
    c) electromagnetically polarized waves are transmitted onto the substrate which is provided with said anchored atoms or molecules,
    d) the waves, reflected by the substrate which is provided with said anchored atoms or molecules, or beamed through, are received,
    e) at least a part of the state of polarization of the received waves is evaluated,
    f) a change in the state of polarization in comparison to a reference sample is acquired, and by way of the evaluated reference values the number and/or type of coupled atoms or molecules is determined without use of an interference film;
    wherein step f) comprises the steps of:
    direct or indirect measuring the optical anisotropy before molecules from said sample have locked but after the surface is coated with receptor molecules;
    direct or indirect measuring optical anisotropy for a different number of locked molecules from said sample;
    using the measured values to calculate the evaluated reference values.

3. The method according to claim 1 wherein the electromagnetic waves are formed by polarized light of a laser.

4. The method according to claim 1, wherein after said anchoring said atoms or molecules on the substrate, said substrate is then washed to remove excess, non-bound atoms and/or molecules.

5. The method according to claim 1, wherein the substrate, after coupling said atoms or molecules to be measured, is washed to remove excess material.

6. The method according to claim 1, wherein it is effected under the application of an ellipsometer.

7. The method according to claim 1, wherein the molecules anchored on said substrate are antigens or antibodies.

8. The method according to claim 1, wherein the method is used for detecting immune globulins and wherein the atoms or molecules anchored on said solid or fluid flat substrate specifically bind said immune globulins.

9. The method according to claim 1, wherein the method is used for detecting auto-immune antibodies and wherein the atoms or molecules anchored on said solid or fluid flat substrate specifically bind said Auto-immune antibodies.

10. The method according to claim 1, wherein the method is used for detecting proteins or peptides and wherein the atoms or molecules anchored on said solid or fluid flat substrate specifically bind said proteins and peptides.

11. The method according to claim 1, wherein the method is used for detecting DNA's and wherein the atoms or molecules anchored on said solid or fluid flat substrate specifically bind said DNA.

12. The method according to claim 1, wherein the method is used for detecting RNA's and wherein the atoms or molecules anchored on said solid or fluid flat substrate specifically bind said RNA.

13. The method according to claim 1, wherein the method is used for detecting receptors or their activators on/in biological membranes wherein the atoms or molecules anchored on said solid or fluid flat substrate specifically bind said receptors or said activators.

14. The method according to claim 1, wherein the method is used for detecting molecules and their bonding partners on/in artificial membranes.

15. The method according to claim 1, wherein said method further comprises the step of using ellipsometry for determining the type and/or quantity of biological and chemical reactants.

16. The method according to claim 1, wherein the reference values are used as a threshold value for a coupling reaction.

17. The method according to claim 1, wherein the method is applied for detecting DNA's or RNA's, wherein the reference values merely take over the function of defining whether a coupling reaction has taken place or not, and wherein the atoms or molecules anchored on said solid or fluid flat substrate specifically bind said DNA or said RNA.

18. The method according to claim 1, wherein for changing the sensitivity of the method, additionally a coupling between the molecules or atoms to be determined and other molecules or atoms is used; wherein said coupling comprises an affinity between molecules that are bound together.

19. A method for the quantitative and/or qualitative determination of atoms or molecules from a sample, wherein the following method steps are to be carried out after one another:

a) atoms or molecules are anchored on a solid or fluid flat substrate, these atoms or molecules being able to selectively bind other molecules or atoms, b) electromagnetically polarized waves are transmitted onto the substrate which is provided with said anchored atoms or molecules, c) the waves, reflected by the substrate which is provided with said anchored atoms or molecules, or beamed through, are received, d) at least a part of the state of polarization of the received waves is evaluated, e) the substrate with said anchored atoms or molecules anchored thereon, for coupling of said atoms or molecules from said sample to be measured, is exposed to said sample atoms or molecules from said sample, f) the method steps b) to d) are again carried out, the change in the state of polarization in comparison to that previously evaluated is acquired, and by way of the evaluated reference values the number and/or type of coupled atoms or molecules is determined.

20. The method according to claim 1, wherein it is effected under the application of an ellipsometer.

* * * * *